US011944670B2

(12) United States Patent
Sirogane et al.

(10) Patent No.: US 11,944,670 B2
(45) Date of Patent: *Apr. 2, 2024

(54) THERAPEUTIC AGENT FOR DISC HERNIATION

(71) Applicant: Seikagaku Corporation, Tokyo (JP)

(72) Inventors: Taiichi Sirogane, Tokyo (JP); Takao Murayama, Tokyo (JP); Masafumi Yaguchi, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 111 days.

This patent is subject to a terminal disclaimer.

(21) Appl. No.: 17/589,162

(22) Filed: Jan. 31, 2022

(65) Prior Publication Data

US 2022/0160845 A1 May 26, 2022

Related U.S. Application Data

(60) Continuation of application No. 16/368,159, filed on Mar. 28, 2019, now Pat. No. 11,266,725, which is a continuation of application No. 15/260,286, filed on Sep. 8, 2016, now Pat. No. 10,286,046, which is a continuation of application No. 14/491,792, filed on Sep. 19, 2014, now Pat. No. 9,463,225, which is a division of application No. 13/993,919, filed as application No. PCT/JP2011/006938 on Dec. 13, 2011, now abandoned.

(30) Foreign Application Priority Data

Dec. 13, 2010 (JP) ................................. 2010-277490

(51) Int. Cl.
*A61K 38/51* (2006.01)
*A61K 9/00* (2006.01)
*A61K 9/19* (2006.01)
*A61K 38/47* (2006.01)
*A61K 47/10* (2017.01)

(52) U.S. Cl.
CPC ............ *A61K 38/51* (2013.01); *A61K 9/0085* (2013.01); *A61K 38/47* (2013.01); *C12Y 402/02004* (2013.01); *A61K 9/0019* (2013.01); *A61K 9/19* (2013.01); *A61K 47/10* (2013.01); *C12Y 402/0202* (2013.01); *C12Y 402/02021* (2013.01)

(58) Field of Classification Search
None
See application file for complete search history.

(56) References Cited

U.S. PATENT DOCUMENTS

| | | | |
|---|---|---|---|
| 4,696,816 A | 9/1987 | Brown | |
| 5,496,718 A | 3/1996 | Hashimoto et al. | |
| 6,007,810 A | 12/1999 | Ishikawa et al. | |
| 6,063,378 A | 5/2000 | Nohara et al. | |
| 2002/0106362 A1* | 8/2002 | Masuda ............ | A61K 38/1841 424/94.1 |
| 2008/0145352 A1 | 6/2008 | Huang et al. | |
| 2013/0266555 A1 | 10/2013 | Sirogane et al. | |
| 2015/0071896 A1 | 3/2015 | Sirogane et al. | |
| 2017/0000863 A1 | 1/2017 | Sirogane et al. | |

FOREIGN PATENT DOCUMENTS

| | | |
|---|---|---|
| DE | 10308885 A1 | 9/2004 |
| EP | 0 576 294 A2 | 12/1993 |
| EP | 0576294 A2 | 12/1993 |
| EP | 0900569 A2 | 3/1999 |
| EP | 2653168 A1 | 10/2013 |
| KR | 10-1692517 B1 | 1/2017 |
| RU | 2 144 833 C1 | 1/2000 |
| RU | 2144833 C1 | 1/2000 |
| RU | 2209080 C2 | 7/2003 |
| WO | 2009128446 A1 | 10/2009 |
| WO | 2012/081227 A1 | 6/2012 |

OTHER PUBLICATIONS

Decision on Grant issued in corresponding Russian application Ser. No. 2013132566/15(048646), dated Dec. 13, 2011, pp. 1-7.
English translation of Decision on Grant issued in corresponding Russian application Ser. No. 2013132566/15 (048646), dated Dec. 13, 2011, pp. 1-5.
Wilke, Hans-Joachim, et al., "Are Sheep Spines a Valid Biomechanical Model for Human Spines?", Spine, vol. 22, No. 20, Feb. 17, 1997, pp. 2365-2374.
Alini, Mauro, et al., "Are animal models useful for studing human disc disorders/degeneration?", Eur Spine J (2008) 17:2-19.

(Continued)

*Primary Examiner* — Michelle F. Paguio Frising
(74) *Attorney, Agent, or Firm* — GREENBLUM & BERNSTEIN, P.L.C.

(57) ABSTRACT

The present invention provides a therapeutic agent for disc herniation, which has extremely few adverse side effects, can achieve a prolonged pain-ameliorating effect when administered in only a single dose, and can exhibit a high therapeutic effect and high safety in clinical applications. The present invention relates to a therapeutic agent for disc herniation, which is characterized by containing chondroitinase ABC as an active ingredient and being administered in such a manner that the ingredient can be administered into a human disk in an amount of 1-8 units per disk.

22 Claims, 3 Drawing Sheets

(56) References Cited

OTHER PUBLICATIONS

Beckstein, Jesse C., et al., "Comparison of Animal Discs Used in Disc Research to Human Lumbar Disc", Spine, vol. 33, No. 6, pp. E166-E173 (2008).
Teh, J., et al., "Diagnostic and Therapeutic Percutaneous Procedures in the Spine", Rivista di Neuroradiologia 17: 362-368, 2004.
Boyd, Lawrence M., et al., "Injectable biomaterials and vertebral endplate treatment for repair and regeneration of the intervertebral disc", Eur Spine J (2006) 15 (Suppl. 3):S414-S421.
U.S. Department of Health and Human Services, Food and Drug Administration, Center for Devices and Radiological Health, "Guidance Document for the Preparation of IDEs for Spinal Systems", Jan. 13, 2000, pp. 1-32.
Manchikanti, Laxmaiah, et al., "A Systematic Review of Mechanical Lumbar Disc Decompression with Nucleoplasty", Pain Physician 2009; 12:561-575, ISSN 1533-3159.
Soderquist, Ryan G., et al., "Central nervous system delivery of large molecules: challenges and new frontiers for intrathecally administered therapeutics", Expert Opin Drug Deliv. Mar. 2010; 7(3): 285-293, doi: 10.1517/17425240903540205.
Friedrich-Freksa, M., et al., "Cystectomy and urinary diversion in the treatment of bladder cancer without artificial respiration", Int Braz J. Urol. 2012; 38: 645-51.
Risbud, Markarand V., et al., "Role of Cytokines in Intervertebral Disc Degeneration: Pain and Disc-content", Nat Rev Rheumatol. Jan. 2014; 10(1): 44-56, doi: 10.1038/nrrheum.2013.160.
Takahashi, T., "Treatment of Lumbar Intervertebral Disc Displacement with Chondroitinase ABC—Experimental Basis for Clinical Application", Clinical Calcium, vol. 14, No. 7, 2004, pp. 85-89.
Moridaira, H., "Long term effects of chondroitinase ABC on porcine intervertebral discs", Orthopaedic Surgery, Hokkaido University Graduate School of Medicine, 78(4), 357-364, 2003.
Iwaya, D., "Action of Chondroitinase ABC as an Agent for Chemonucleolysis in Non-Human Primate", International Intradiscal Therapy Society, Inc., Ninth Annual Meeting, May 8-12, 1996, Amsterdam, Holland.
Nordby, E., et al., "Letters", Spine, 1997, vol. 22, No. 18, pp. 2194-2195.
Yamada, K., et al., "Investigation of the Short-Term Effect of Chemonucleolysis with Chondroitinase ABC", The Journal of Veterinary Medical Science/the Japanese Society of Veterinary Science, (May 2001), vol. 63, No. 5, pp. 521-525.
Brown, Mark D., "The rationale for pre-clinical results of chondroitinase ABC in chemonucleolysis", International Congress Series, vol. 1223, Dec. 2001, pp. 171-176.
Ishikawa, H., et al., "Action of Chondroitinase ABC on Epidurally Transplanted Nucleus Pulposus in the Rabbit", Spine, vol. 24, No. 11, pp. 1071-1076.
Sumida, K., et al., "Serial Changes in the Rate of Proteoglycan Synthesis After Chemonucleolysis of Rabbit Intervertebral Discs", Spine, vol. 24, No. 11, pp. 1066-1070.
Ono, A., et al., "Proteoglycans in the Nucleus Pulposus of Canine Intervertebral Discs After Chondroitinase ABC Treatment", Journal of Spinal Disorders, 1998, vol. 11, No. 3, pp. 253-260.
Lu, D, et al., "Effects of Chondroitinase ABC and Chymopapain on Spinal Motion Segment Biomechanics", Spine, 1997, vol. 22, No. 16, pp. 1828-1835.
Takahashi, T., et al., "Treatment of Canine Intervertebral Disc Displacement With Chondroitinase ABC", 1997, Spine, vol. 22, No. 13, pp. 1435-1439.
Olmarker, K., et al., "Microvascular Effects of Chondroitinase ABC and Chymopapain", Clinical Orthopaedics and Related Research, Aug. 1990, No. 257, pp. 274-279.
Olmarker, K., et al., "Chodroitinase ABC (Pharmaceutical Grade) for Chemonucleolysis", Spine, Sep. 1996, vol. 21, No. 17, pp. 1952-1956.
Lu, D., "Biomechanical, Radiological and Histological Studies of the Canine Lumbar Intervertebral Disc after Chemonucleolysis-Comparison of Chondroitinase-ABC and Chymopapain", Hokkaido Journal of Orthopedic and Traumatic Surgery, 1997, vol. 40, No. 1, pp. 29-36.
Sakuma, M., et al., "Effect of Chondroitinase ABC on Matrix Metalloproteinases and Inflammatory Mediators Produced by Intervertebral Disc of Rabbit In Vitro", Spine, Mar. 2002, vol. 27, No. 6, pp. 576-580.
Decision on Grant issued in corresponding Russian Application No. 2013132566/15, dated Dec. 13, 2011, 7 pages.
English translation of Decision on Grant issued in corresponding Russian Application No. 2013132566/15, dated Dec. 13, 2011, 5 pages.
Sasaki et al., "Effects of chondroitinase ABC on intradiscal pressure in sheep: An in vivo study", Spine 2001, vol. 26, pp. 463-468.
Takahashi et al., "Chemonucleolytic effects of chondroitinase ABC on normal rabbit intervertebral discs", Spine 1996, vol. 21, pp. 2405-2411.
Smith, Lyman, "Enzyme Dissolution of the Nucleus Pulposus in Humans", Preliminary Communication, vol. 187, No. 2, 1964, pp. 137-140.
Dotzel, Margaret; Federal Register, vol. 68, No. 17, Monday Jan. 27, 2003.
Matsuyama, Yukihiro, "Intradiscal Therapy for Low Back Pain", Clinical Orthopaedic Surgery, vol. 42, No. 3, pp. 223-228 (2007).
Fry, et al., "Radiographic and Histologic Effects of Chondroitinase ABC on Normal Canine Lumbar Intervertebral Disc", Spine, vol. 16, No. 7, pp. 816-819 (1991).
Mochida et al., "The Importance of Preserving Disc Structure in Surgical Approaches to Lumbar Disc Herniation", Spine, vol. 21, No. 13, pp. 1556-1563 (1996).
Alini et al., "Are animal models useful for studying human disc disorders/degeneration?" Eur. Spine J., vol. 17, pp. 2-19 (2008).
Supplemental European Search Report dated May 26, 2014 issued in corresponding European Application No. EP11848463.
Sugimura, et al., Experimental Chemonucleolysis with Chondroitinase ABC in Monkeys, Spine, vol. 21, No. 2, pp. 161-165, Jan. 15, 1996 (XP0992989597).
English Translation of IPRP issued in corresponding International Application No. PCT/JP2011/006938, dated Jun. 18, 2014.
English language translation of first Office Action issued in corresponding Korean application KR 10-2016-7036791, dated Mar. 6, 2017, 5 pages.
First Office Action issued in corresponding Korean application KR 10-2016-7036791, dated Mar. 6, 2017, 6 pages.
Hearing Notice cited in corresponding Indian Application No. 5431/CHENP/2013 dated Aug. 28, 2020.
Johannessen W, Vresilovic EJ, Seguritan JA, Elliot DM, "Altered Nucleus Pulposus Mechanics Using Chondroitinase-ABC and Genipin as a Model of Early Disc Degeneration", Trans Orthop Res Soc Mar. 7, 2004; 29-1150.
Manchikanti et al. (Jul.-Aug. 2009) "Comprehensive Review of Therapeutic Interventions in Managing Chronic Spinal Pain", Pain Physician, 12(4):E123-E198.
Matsuyama Yukihiro. (2007) "Intradiscal Therapy for Low Back Pain", Clinical Orthopaedic Surgery, 42 (3):223-228.
Tester et al. (Feb. 2008) "Chondroitinase ABC Improves Basic and Skilled Locomotion in Spinal Cord Injured Cats", Experimental Neurology, 209(2):483-496.
2008) High Purity Reagents for Glycobiology & Glycoanalysis, Product & Services Catalog; AMS Biotechnology Ltd, 7 pages.
Office Action dated Apr. 24, 2023 in Chinese family member application No. 201910468925.1, and English language translation thereof.
"Mini-Invasive Techniques for Orthopedic", Yulai Lu et al., p. 248, People's Military Medical Press, Apr. 30, 2010, and English language translation thereof.
"Clinical Medicine", Dianxin Liu et al., p. 438, Heilongjiang Science and Technology Press, Jun. 30, 2009, and English language translation thereof.
Office Action issued to Russian Patent Application No. 2019116210/04/ dated Nov. 21, 2022, along with English translation thereof.

\* cited by examiner

THERAPEUTIC AGENT FOR DISC HERNIATION

CROSS-REFERENCE TO RELATED APPLICATIONS

This application is a Continuation of U.S. application Ser. No. 16/368,159, filed on Mar. 28, 2019, allowed, which is a Continuation of U.S. application Ser. No. 15/260,286, filed on Sep. 8, 2016, patented, which is a Continuation of U.S. application Ser. No. 14/491,792, filed on Sep. 19, 2014, patented, which is a Division of U.S. application Ser. No. 13/993,919, filed on Jun. 13, 2013, abandoned. U.S. application Ser. No. 13/993,919 is a 35 U.S.C. § 371 U.S. national entry of International Application PCT/JP2011/006938 (WO 2012/081227) having an International filing date of Dec. 13, 2011, which claims under 35 U.S.C. § 119(a) the benefit of Japanese Application No. 2010-277490, filed Dec. 13, 2010, the entire contents which are incorporated herein by reference.

TECHNICAL FIELD

The present invention relates to a therapeutic agent for disc herniation containing chondroitinase ABC as an active ingredient.

BACKGROUND ART

Disc herniation is a disease that causes leg pain, low back pain, and the like due to the pressure on nerves of spinal cords, and the like, attributed to protrusion of the disc tissue into the vertebral canal because the nucleus pulposus perforates the anulus fibrosus present therearound. It has been reported that the therapeutic principle is a conservative therapy and approximately 90% of cases have been cured by such a conservative therapy. As the conservative therapy, there have been performed various treatments, such as rest, bed rest, medication (non-steroidal anti-inflammatory drugs (NSAIDs), corticosteroids, muscle relaxants), spinal orthosis (corset), traction therapy, thermotherapy, epidural block, nerve root block, and exercise therapy. If no amelioration is seen in these conservative therapies, a surgical therapy is selected, and surgical operations have been applied to 10-30% of all patients with lumbar disc herniation. In recent years, chemonucleolysis has been designed in order to reduce the invasion and load due to surgery.

Chemonucleolysis is a method of injecting an enzyme into the disc to bring about the nucleolysis of nucleus pulposus and reduce the internal pressure of the disc so that the pressure on the spinal nerve roots is reduced.

So far, a method of using chymopapain as an enzyme to be injected into the disc has been reported, and its effectiveness has been reported in 1964 (Non-Patent Document 1). However, chymopapain also acts on the surrounding tissue of the disc including not only the nucleus pulposus but also the spinal cord, and its sale as a medicine has been discontinued at present because severe neurological complications (paraplegia, transverse myelitis, cerebral hemorrhage, subarachnoid hemorrhage, quadriplegia, etc.) were found (Non-Patent Document 2).

Therefore, any medicines for chemonucleolysis are currently not commercially available and the development of a medicine that is able to safely perform chemonucleolysis has been desired.

It is considered that chondroitinase ABC decomposes the glucosaminoglycan chains of proteoglycans present in the nucleus pulposus (such as chondroitin sulfate chains and hyaluronic acid chains) to reduce the intradiscal pressure due to the reduction in high water retention ability of proteoglycan, resulting in reduction of the pressure on the spinal nerve roots. In addition, unlike chymopapain, it was reported in 1985 that chondroitinase ABC was expected as a safe medicine with almost no injury to such neural tissue surrounding the disc and use of chondroitinase ABC as an enzyme to be injected into the disc was tried (Patent Document 1, Non-Patent Document 3, Non-Patent Document 4).

However, since the disc also has originally a role as a cushion to support the weight applied to the spine, the cushion function that the disc should have originally had is impaired if the nucleus pulposus is removed in excess. In fact, in patients with decreased disc height by at least 30% by surgical treatment, it is shown that there is a possibility of back pain that is persistent (Non-Patent Document 5). Therefore, if the nucleus pulposus undergoes nucleolysis excessively even in chemonucleolysis by administration of chondroitinase ABC, the cushion function of the disc that should have originally had is impaired to result in leading to a possibility of adverse side effects.

In addition, since chondroitinase ABC is a heterologous protein that is not present in humans, it is necessary to succeed in a therapy in only a single dose rather than multiple doses, also from the viewpoint of prevention of anaphylactic shock or the like. Completion of the therapy in a single dose administration means that it is required to show a significant therapeutic effect in only a single dose administration and derive the optimal dose with few adverse side effects because multiple dose administration cannot be performed until a complete recovery.

In addition, a lot of studies on disc degeneration have been carried out in animal models, but more attention and study effort were required to apply the results in animal models to the study of human disk degeneration due to the fact that disks vary among different animal species (Non-Patent Document 6).

The special nature of a single dose administration and the difficulty in applying animal models to humans as described above make chemonucleolysis with chondroitinase ABC difficult, and, in fact, practical use of chondroitinase ABC has not yet been realized even today though 25 years have passed since 1985 described above.

Patent document 1 describes that disc herniation is treated by administering chondroitinase ABC into a disc so that the nucleus pulposus undergoes the nucleolysis and a therapeutic effect on disc herniation was obtained by administering chondroitinase ABC in an amount of 100 units per disk into a human disk. However, its effective dose has not yet been determined because the effect is not sufficient and the investigation on the adverse side effects has not been made. In addition, Non-Patent Document 3 describes that a therapeutic effect on disc herniation was obtained by administering chondroitinase ABC in an amount of 0.5 units per disk into a human disk. Non-Patent Document 4 describes that chondroitinase ABC was administered into a dog disc in an amount of 0.5-1, 2.5-5, and 5-10 units per disk, but when this dose is converted into the dose for humans, it becomes to be about at least 35 units because the volume of human nucleus pulposus is approximately 70 times compared to that of dog nucleus pulposus. However, a detailed study of adverse side effects after administration of chondroitinase ABC has not been carried out.

Therefore, the optimal dose of chondroitinase ABC to show the maximum therapeutic effect and the minimum side effect has neither been disclosed nor suggested.

PRIOR ART DOCUMENT

Patent Document

Patent Document 1: U.S. Pat. No. 4,696,816

Non-Patent Documents

Non-Patent Document 1: Smith L. Enzyme dissolution of the nucleus pulposus in humans. JAMA 1964(2); 187: 137-40.
Non-Patent Document 2: US Federal Register. Monday Jan. 27, 2003; 68(17): 3886-7.
Non-Patent Document 3: Rinsho Seikei Geka (The Journal of the Japanese Clinical Orthopaedic Association) Vol. 42, No. 3, pages 223-228, March, 2007
Non-Patent Document 4: SPINE, 1991; 16(7): 816-19
Non-Patent Document 5: SPINE, 1996; 21(13): 1556-64
Non-Patent Document 6: Eur Spine J, 2008; 17: 2-19

SUMMARY OF THE INVENTION

Problems to be Solved by the Invention

As described above, it has been reported that chondroitinase ABC is useful as an active ingredient of a medicine for chemonucleolysis, but chondroitinase ABC has not yet been put to practical use because serious adverse side effects caused by the excess dissolution of the nucleus pulposus is also concerned and it is unknown whether or not a reliable therapeutic effect can be exhibited in only a single dose and whether or not there is a dose with no adverse side effects.

The problem of the present invention is to provide a therapeutic agent for disc herniation, which has extremely few adverse side effects, can achieve a prolonged pain-ameliorating effect when administered in only a single dose, and can exhibit a high therapeutic effect and high safety in clinical applications.

Means for Solving the Problem

As a result of further intensive studies about the treatment with chondroitinase ABC by the present inventors, it has been surprisingly found that by the administration of chondroitinase ABC in a specific amount, adverse side effects can be reduced and a prolonged pain-ameliorating effect/a high therapeutic effect in clinical applications are exhibited, and thus the present invention has been completed.

That is, it has been found that not only therapeutic effects can be expected but also adverse side effects can be reduced at a dose of 1-8 units of chondroitinase ABC per disk into a human disk, and that an excellent therapeutic agent for disc herniation that uses chondroitinase ABC and is practical can be provided.

The present invention relates to a therapeutic agent for disc herniation, containing chondroitinase ABC as an active ingredient and being administered into a human disk in an amount of 1-8 units per disk.

Also, the present invention relates to a formulation for the treatment of disc herniation, which formulation is used for the administration of chondroitinase ABC into a human disk in an amount of 1-8 units per disk.

In addition, the present invention relates to a method for treating disc herniation, comprising administering a formulation containing, as an effective dose, 1-8 units of chondroitinase ABC to a patient with disc herniation.

More particularly, the present invention is as follows.

(1) A therapeutic agent for disc herniation, which is characterized by containing chondroitinase ABC as an active ingredient and being administered in such a manner that the ingredient can be administered into a human disk in an amount of 1-8 units per disk.

(2) The therapeutic agent according to the above (1), wherein the disc herniation is a lumbar disc herniation.

(3) The therapeutic agent according to the above (1) or (2), wherein the chondroitinase ABC is derived from *Proteus vulgaris*.

(4) A formulation containing chondroitinase ABC for treating disc herniation by the administration into a human disk in an amount of 1-8 units per disk.

(5) The formulation according to the above (4), wherein the formulation is a single dose formulation.

(6) The formulation according to the above (4) or (5), wherein the formulation is an injection.

(7) The formulation according to any one of the above (4) to (6), wherein the disc herniation is a lumbar disc herniation.

(8) A method for treating disc herniation, comprising administering chondroitinase ABC to a human disk of a patient with disc herniation in an effective amount of 1-8 units per disk.

(9) Chondroitinase ABC for use as a therapeutic agent for disc herniation, which is characterized by being used in such a manner that it can be administered into a human disk in an amount of 1-8 units per disk.

Effects of the Invention

In accordance with the present invention, there can be provided a therapeutic agent for disc herniation, which has fewer adverse side effects, is able to complete the therapy of disc herniation in only a single dose, is safe, has a high therapeutic effect and a high clinical usefulness, and is highly practical.

The present invention is intended to clarify for the first time the existence of a dose that is safe and has a high therapeutic effect as well as a clinical usefulness in chemonucleolysis with chondroitinase ABC and also clarify for the first time the limited range of the dose including 1-8 units, preferably 1-5 units, contributing much to a practical use of chemonucleolysis by the administration of chondroitinase ABC.

MODES FOR CARRYING OUT THE INVENTION

Figure 1:
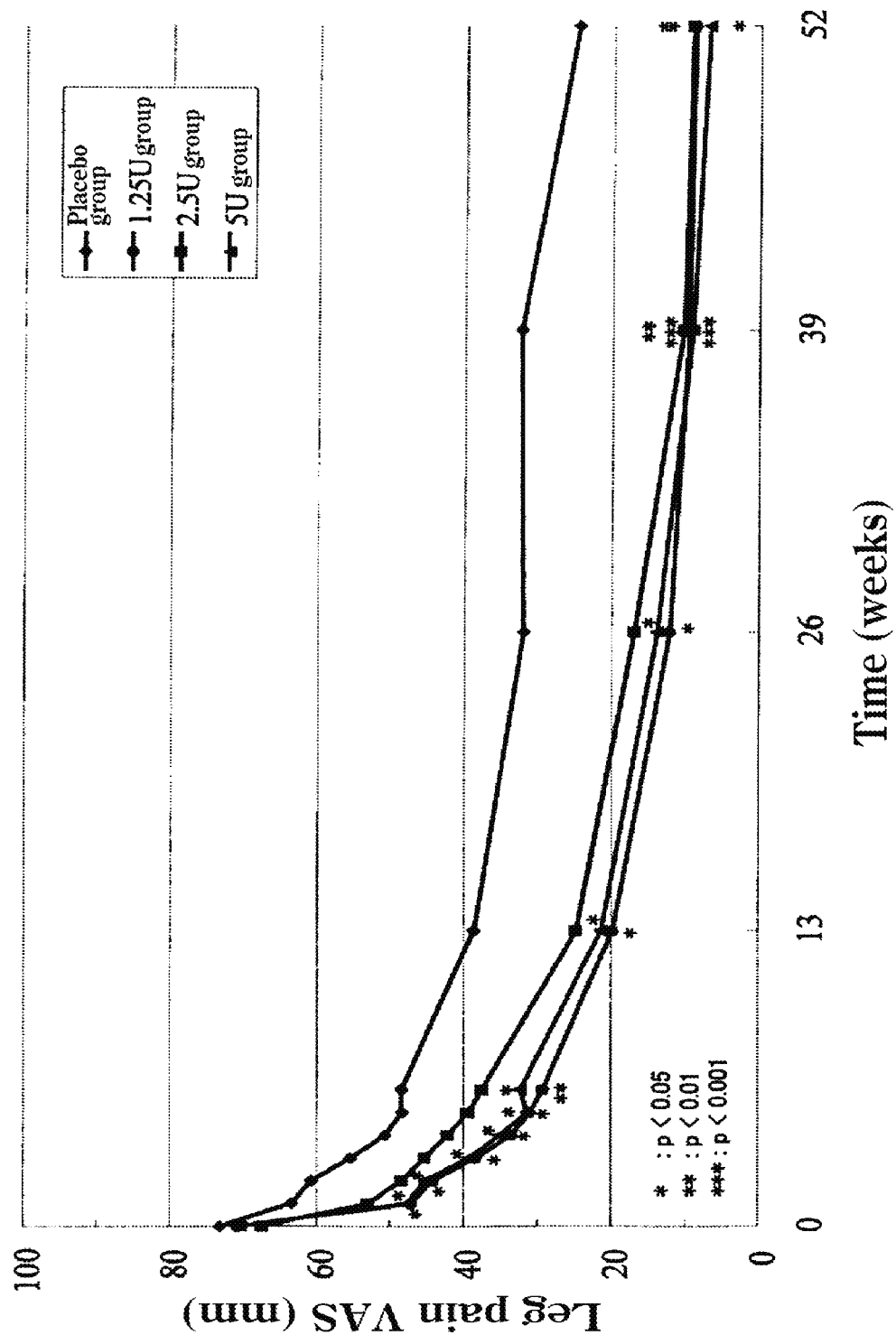
FIG. 1 is a graph showing the transition of leg pain at the worst time (VAS) after administration of a therapeutic agent.

The following describes embodiments of the present invention.

(1) Active Ingredient of the Therapeutic Agent of the Present Invention

Chondroitinase ABC used as an active ingredient for the therapeutic agent of the present invention is not particularly limited as long as it is an enzyme having an action of chondroitinase ABC. Although its origin is also not particularly limited, chondroitinase ABC is preferably derived from microorganisms and preferably derived from *Proteus vulgaris*.

The method for manufacturing such chondroitinase ABC is also not particularly limited, and chondroitinase ABC may be manufactured, for example, by culturing a microorganism such as *Proteus vulgaris* and the like or by genetic engineering techniques using a DNA encoding the chondroitinase ABC.

Chondroitinase ABC as such is preferably an enzyme which is purified to the extent that can be used as a medicine and does not contain any medically unacceptable contaminants.

More specifically, such chondroitinase ABC has an enzymatic activity of 270 units/mg protein or more and contains endotoxin, nucleic acid, and protease in amounts not more than the respective detection limits. Such chondroitinase ABC can be obtained by, for example, the method as described in JP 6-153947-A.

Further, in the present invention, "1 unit" of chondroitinase ABC is referred to as the amount of enzyme liberating 1 micromole (M) of unsaturated disaccharide per minute when the enzyme was allowed to react with chondroitin sulfate C as a substrate at pH 8.0 and 37° C.

When chondroitinase ABC having an enzymatic activity of 270 units/mg protein or more is used, proteoglycan at the targeted site can be appropriately degraded without affecting tissues around the targeted site by administering it to a living body as an injectable pharmaceutical preparation. Thus, the enzyme can be a safe and effective medicine.

(2) Target Disease

Target disease of the therapeutic agent of the present invention is not limited as long as it is disc herniation, and such a target disease is preferably a lumbar disc herniation, and especially preferably, among these, a lumbar disc herniation occurring in the disc between the fourth lumbar vertebra and the fifth lumbar vertebra, or in the disc between the fifth lumbar vertebra and the first sacrum.

(3) Administration Site/Method/Frequency

The therapeutic agent of the present invention is used to inject into the nucleus pulposus present within the disc where disc herniation occurs. The frequency of the injection is once.

Chondroitin sulfate chains and hyaluronic acid chains in the nucleus pulposus of the disc are degraded by this injection so that the high water retention ability of proteoglycans is attenuated to result in reduction of the intradiscal pressure, leading to reduce the pressure on spinal nerve roots due to disc herniation, thereby to ameliorate disc herniation.

(4) Dose

Chondroitinase ABC that is the active ingredient of the therapeutic agent of the present invention is administered at a dose of 1-8 units per disk. Of these, 1-6 units are preferably administered, 1-5 units are more preferably administered, 1-3 units are more preferably administered, 1-2.5 units or 1.25-3 units are further preferably administered, 1.25-2.5 units are especially preferably administered, and 1.25 units or 2.5 units are most preferably administered.

Figure 2:
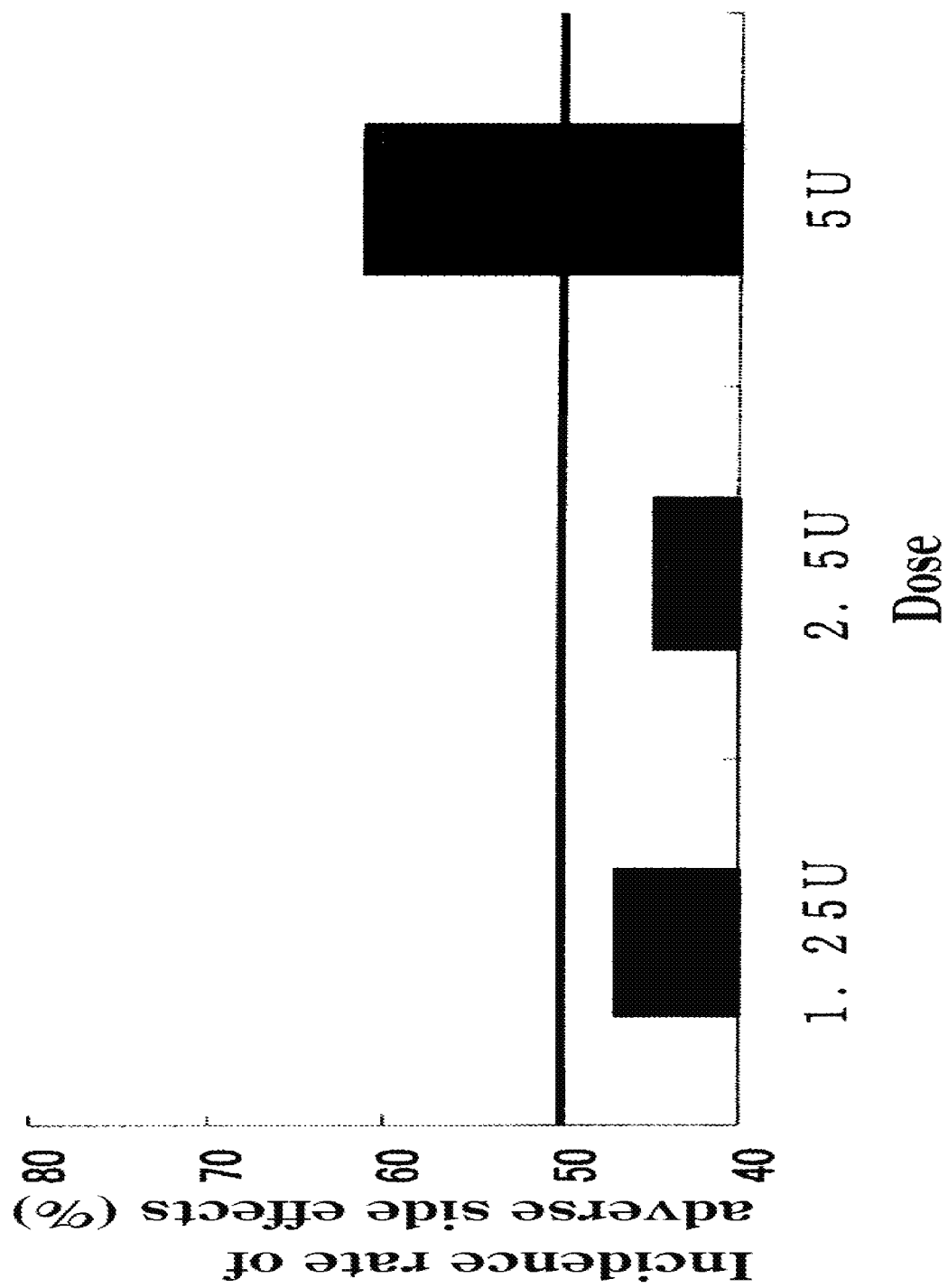
FIG. 2 is a graph showing the incidence rate of adverse side effects per administration group of each unit.

In particular, at a dose of 1.25-5 units, the therapeutic effect is almost the same (see FIG. 1), and the incidence rate (%) of adverse side effects is minimal at a dose of 2.5 units (see FIG. 2). Thus, 1-5 units, preferably 1-3 units are required in order to ensure the effective therapeutic effect and safety in only a single dose.

(5) Dosage Form, Etc

The therapeutic agent of the present invention can be provided in a dosage form that is usually employed as an injection. For example, the dosage form may be any of a solution form, a frozen form, and a freeze-dried form. An injection can be prepared by filling this into an appropriate container such as ampoules, vials, syringes for injections, etc. and sealing the container.

Further, when filling or sealing the therapeutic agent of the present invention in a suitable container, such as ampoules, vials, and syringes for injection, in order to prevent a chemical reaction of the therapeutic agent of the present invention, especially oxidation, the container may be filled or sealed together with an inert gas such as nitrogen gas and rare gas.

The material of the container such as ampoules, vials, and syringes for injections, which is able to fill and seal the therapeutic agent of the present invention, is not particularly limited as long as it does not affect the therapeutic agent of the present invention and is a pharmaceutically acceptable material.

It is possible to use known methods for formulation of the therapeutic agent of the present invention. In the formulation, other pharmaceutically active ingredients and ingredients usually used in medicines, such as conventional excipients, stabilizers, binders, emulsifiers, osmotic agents, buffers, pH regulators, isotonic agents, preservatives, soothing agents, colorants, or the like may be used as long as they do not adversely affect the activity of chondroitinase ABC itself and do not adversely affect the action of chondroitinase ABC.

EXAMPLES

Hereinafter, the present invention will be described in more detail by way of Examples, but these are illustrative of the present invention and the scope of the present invention is not intended to be limited thereto.

Example 1

Production of Therapeutic Agent of the Present Invention (1) Production of Chondroitinase ABC Chondroitinase ABC was produced by culturing *Proteus vulgaris* and purifying the culture supernatant according to the method described in JP 6-153947-A.

The respective enzyme activities of chondroitinase ABC produced were all in the range of 270-480 units/mg protein. In addition, the contents of endotoxin, nucleic acid, and protease in chondroitinase ABC were all equal to or below the detection limit.

(2) Formulation

The following three kinds of freeze-dried injectable formulations (A) to (C) containing the chondroitinase ABC having the following each unit and the following formulation ingredients.

(A) The chondroitinase ABC of 5 units
(B) The chondroitinase ABC of 10 units
(C) The chondroitinase ABC of 20 units
Formulation Ingredients:

| | |
|---|---|
| Sodium hydrogen phosphate hydrate | 1.125 mg |
| Sodium dihydrogen phosphate | 0.3 mg |
| Sucrose | 5 mg |
| Polyethylene glycol 3350 | 10 mg |

(Note: Polyethylene glycol 3350 corresponds to macrogol 4000 listed in the Japanese Pharmacopoeia.)

Further, a freeze-dried injectable formulation containing only the formulation ingredients (not containing chondroitinase ABC) prepared in the same manner was used as a placebo.

(3) Dissolution Before Administration

A ready-to-use solution (4 mL) having the following composition was added to each formulation of (A) to (C) (including a placebo) described above before use, so that the formulations were dissolved to prepare a formulation of 1.25 units/mL for administration, a formulation of 2.5 units/mL for administration, and a formulation of 5 units/mL for administration, respectively. A placebo formulation was prepared in the same manner.

Ready-to-Use Solution:

| | |
|---|---|
| Sodium hydrogen phosphate hydrate | 3.375 mg |
| Sodium dihydrogen phosphate | 0.9 mg |
| Sucrose | 15 mg |
| Polyethylene glycol 3350 (corresponding to macrogol 4000 listed in the Japanese Pharmacopoeia) | 30 mg |
| Sodium chloride | 36 mg |
| Water for injection | 4 ml |

Example 2

Study on Patients with Disc Herniation

1. Subjects

Japanese patients (194 cases in total) with the age of 20-70 years and with the following lumbar disc herniation were served as the subjects:

patients with protrusion herniation or subligamentous extrusion herniation (not protruding into the posterior longitudinal ligament), in whom a lumbar disc herniation occurring in the disc between the fourth lumbar vertebra and the fifth lumbar vertebra or in the disc between the fifth lumbar vertebra and the first sacrum was confirmed by MRI and clinical symptoms were consistent with the location of the damaged nerve roots; and patients in the case where a sixth lumbar vertebra is observed and in whom the fifth lumbar nerve root or the first sacral nerve root is damaged and clinical symptoms are consistent with the location of the damaged nerve roots.

The above subjects were divided into each group of a placebo administration group (47 subjects), an administration group of 1.25 units of chondroitinase ABC (49 subjects), an administration group of 2.5 units of chondroitinase ABC (49 subjects) and an administration group of 5 units of chondroitinase ABC (49 subjects), and corresponding formulations as described above were administered respectively.

2. Method for the Administration of the Therapeutic Agent of the Present Invention Of each formulation (4 ml) for the administration as described in Example 1, 1 ml of such a formulation was used for the administration. Therefore, the amount of the enzyme which is to be administered is 1.25 units/mL in the case of the formulation for the administration of 1.25 units, 2.5 units/mL in the case of the formulation for the administration of 2.5 units, and 5 units/mL in the case of the formulation for the administration of 5 units.

Using these formulations, a single dose of 1 ml each was injected into the nucleus pulposus of the disc as shown below.

3. Evaluation (1) Pharmacological Evaluation (a) Pain Evaluation by the Subject (Visual Analog Scale: VAS)

At each time point of 1 week, 2 weeks, 3 weeks, 4 weeks, 5 weeks, 6 weeks, 13 weeks, 26 weeks, 39 weeks and 52 weeks after administration of the formulation, a measurement about "the worst leg pain during the past 24-hour period (VAS evaluation)" that was evaluated by the subject oneself was performed (a measurement of the VAS value).

The VAS evaluation by the subject was performed before bedtime. On a 100 mm straight line of "a pain evaluation sheet" in which "no pain" is described on the left end of the straight line and "biggest pain felt in the past" is described on the right end, the degree of pain was marked with a point by the subject oneself.

The distance (mm) of from the left end of the same straight line to the point where the subject had marked was measured to evaluate the degree of pain. The results of this evaluation were analyzed by a Dunnett type multiple comparison test using a placebo group as a control.

In addition, the rate of change in pain (rate of change in VAS) was evaluated. The rate of change in VAS was determined by obtaining a VAS variation by subtracting the VAS value at 13 weeks after administration of the formulation from the VAS value before administration of the formulation, and dividing the VAS variation by the VAS value before administration of the formulation. A covariance analysis (p<0.05) was performed for this VAS variation, using a placebo group as a control.

(b) Neurological Examination

A straight leg raising test (SLR test) was performed at week 13 after administration of the formulation, in order to examine the nerve stimulation caused by disc herniation.

The SLR test is one of the neurological examinations of lumbar disc herniation, and when the lower limbs were stretched, the case where the straight leg raising angle is 70 degrees or less is determined to be "positive" and the case where the straight leg raising angle exceeds 70 degrees is determined to be "negative". Before administration of the formulation in this study, all subjects were positive.

The frequency of the positive and negative cases in the SLR test for each group was summed up, and the ratio of negative cases in the SLR test was examined by a Steel-type multiple comparison using a placebo group as a control.

In addition, an evaluation of drug efficacy was carried out in 193 cases of the target subjects.

(2) Safety Evaluation

A safety evaluation was carried out in 194 cases of the target subjects.

The number of appearance and the incidence rate of adverse side effects were determined. The evaluation was carried out until 13 weeks after administration of the formulation. However, among the adverse side effects, the following items of (a) and (b) were evaluated until 52 weeks after the administration;

when compared to the value before administration of the formulation, (a) the cases in which the reduction rate of the disc height was equivalent to or more than 30% after such administration, and (b) the cases in which the vertebral posterior angle of the vertebral body was equivalent to or more than 5 degrees.

In addition, the safety evaluation of the item (b), such that the vertebral posterior angle of the vertebral body should be equivalent to or more than 5 degrees, is an index related to the instability of the disc, which is established by The U.S. Food and Drug Administration (FDA).

The average reduction rate of the disc height in an administration group receiving each unit was determined 13 weeks after the administration of the formulation.

4. Result (1) Pharmacological Evaluation (a) VAS

FIG. 1 shows transition of the worst leg pain (VAS) after administration of the formulation. The horizontal axis of FIG. 1 shows the time (weeks) after the administration, and the vertical axis shows the value (mm) of VAS. The rhomboid mark (♦) in the graph shows the results of the placebo group, the black circle mark (●) shows the results of an administration group of 1.25 units of chondroitinase ABC, the square mark (■) shows the results of an administration group of 2.5 units of chondroitinase ABC, and the black triangle mark (▲) shows the results of an administration group of 5 units of chondroitinase ABC.

A pain-inhibitory effect was observed from the first week in any of the administration groups of the formulations. In particular, a significant pain-inhibitory effect ($p<0.05$) was observed from the first week in the administration group of the formulation of 1.25 units of chondroitinase ABC, and the administration group of the formulation of 5 units of chondroitinase ABC, compared to the placebo group. In addition, at weeks 39 and 52 after administration, a significant pain-inhibitory effect ($p<0.01$ or $p<0.001$) was shown in all the administration groups, compared to the placebo group. The pain-inhibitory effects are substantially equal in the administration group of 1.25 units, the administration group of 2.5 units, and the administration group of 5 units, and it was shown that such inhibitory effect was effective over a one year (52 weeks). As a result, it was demonstrated that a single administration of the formulation showed a significant pain-inhibitory effect.

In addition, the rate of change in VAS at week 13 after the administration was 66% in the administration group of 1.25 units of chondroitinase ABC, 61% in the administration group of 2.5 units of chondroitinase ABC, and 69% in the administration group of 5 units of chondroitinase ABC, and a significant reduction in the rate of change in VAS was confirmed in any of the administration groups of the above units, compared to that (45%) of the placebo administration group.

(a) Neurological Examination (SLR Test)

The negative rate in the placebo group was about 50%, but the negative rates in the administration groups were all 60% or more. In particular, the negative rate in the administration group of 1.25 units of chondroitinase ABC has reached 80% or more.

In any administration groups, there was an increase in the proportion of negative response. Particularly, the proportion of negative response was significantly increased ($p<0.01$) in the administration group of 1.25 units of chondroitinase ABC, compared to the placebo administration group.

(2) Safety Evaluation

The incidence rate of adverse side effects is shown in FIG. 2. The horizontal axis in FIG. 2 shows each administration group, and the vertical axis shows the incidence rate (%) of adverse side effects. The incidence rate of adverse side effects in the administration group of 5 units of chondroitinase ABC was 61.2%, 44.9% in the administration group of 2.5 units of chondroitinase ABC, and 46.9% in the administration group of 1.25 units of chondroitinase ABC. From this, it was shown that the minimum value of the incidence rate of adverse side effects was in the vicinity of 2.5 units per disk for the administration group and the presence of a dose being able to cause minimal adverse side effects was clarified.

Then, adverse side effects as the instability of the disc were studied on (a) the cases where the vertebral posterior angle of the vertebral body was equivalent to or more than 5 degrees and (b) the cases where the average reduction rate of the disc height was equal to or more than 30%. The results are shown in Table 1 below.

TABLE 1

| Administration group | Placebo group N = 47 | 1.25U group N = 49 | 2.5U group N = 49 | 5U group N = 49 | 10U group N = 6 |
|---|---|---|---|---|---|
| Vertebral posterior angle of vertebral body | 0 (0%) | 0 (0%) | 0 (0%) | 1 (2.0%) | 2 (33.3%) |
| Reduction in disc height | 0 (0%) | 4 (8.2%) | 4 (8.2%) | 7 (14.3%) | — |

— : No data

As a result, 1 case (2% incidence rate) where the vertebral posterior angle of the vertebral body was 5 degrees or more was observed in the administration group of 5 units of chondroitinase ABC. On the other hand, there was no case where the vertebral posterior angle of the vertebral body was 5 degrees or more in the administration group of 1.25 units of chondroitinase ABC and in the administration group of 2.5 units of chondroitinase ABC. Further, in the administration group of 10 units of chondroitinase ABC as a comparative example, 2 cases (33.3% incidence rate) where the vertebral posterior angle of the vertebral body was 5 degrees or more were observed, indicating that adverse side effects related to the instability of the disc occurred in a high percentage, which was of no practical use.

There were 7 cases (14.3% incidence rate), where the reduction rate in the disc height was 30% or more, in the administration group of 5 units of chondroitinase ABC, 4 cases (8.2% incidence rate) in the administration group of 1.25 units of chondroitinase ABC, and 4 cases (8.2% incidence rate) in the administration group of 2.5 units of chondroitinase ABC. The occurrence of the adverse side effects was found to be decreased rapidly.

Figure 3:
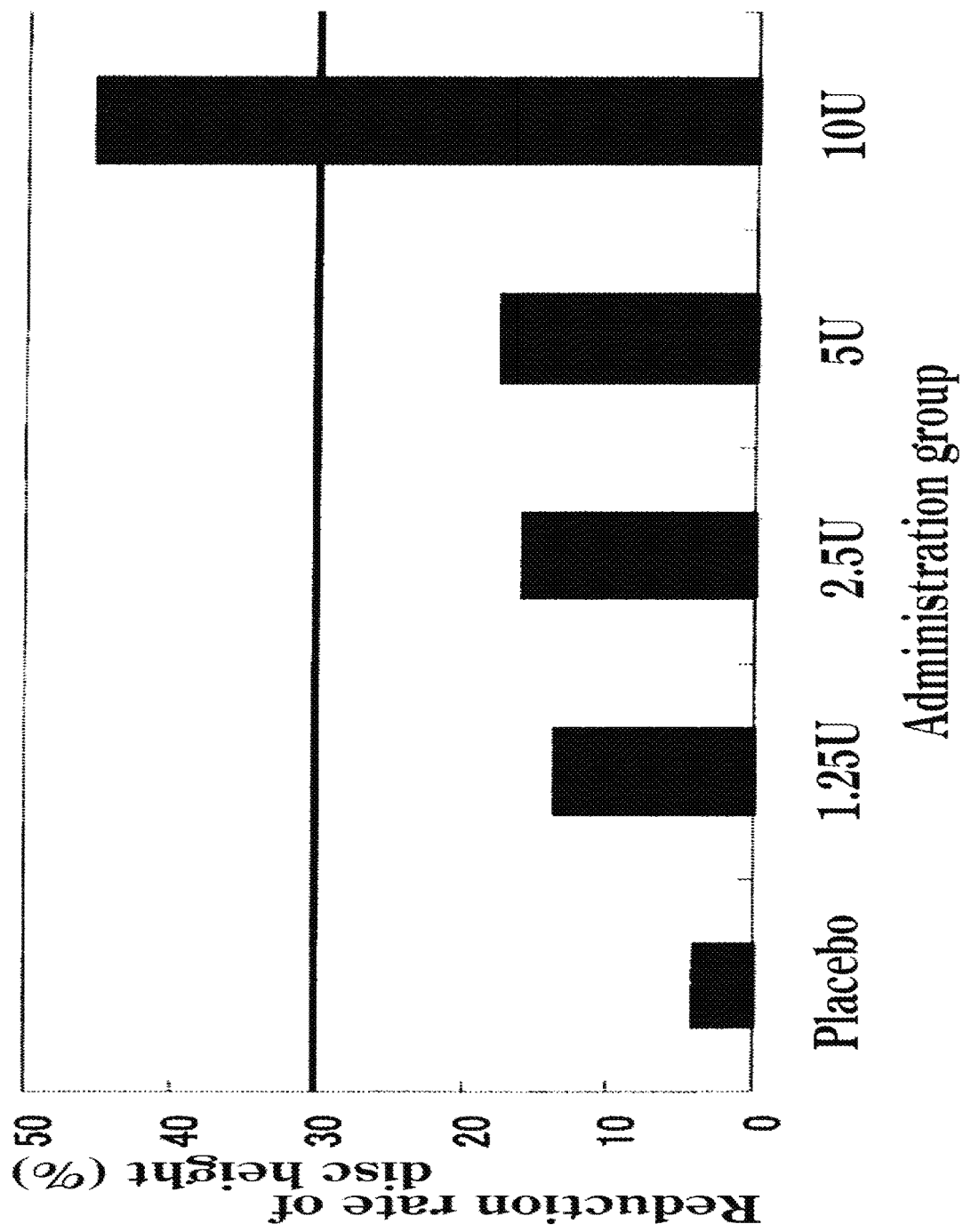
FIG. 3 is a graph showing the average reduction rate for the disc height per administration group of each unit.

Next, the average reduction rate of the disc height in the administration groups of each unit is shown in FIG. 3. The horizontal axis in FIG. 3 shows each administration group, and the vertical axis shows the reduction rate (%) of the disc height.

As a result, it was found that the average reduction rates of the disc height in the administration groups of 5 units, 2.5 units, and 1.25 units of chondroitinase ABC were all less than 30%. These administration groups each showed a great reduction rate of the disc height compared to the placebo group, and it was shown that a therapeutic effect was observed. In addition, in the administration group of 10 units of chondroitinase ABC in Comparative Example, the reduction rate was found to be 30% or more.

In addition, an increase in IgG antibody titer against chondroitinase ABC, which is a side effect, was observed in 1 case in the administration group of 2.5 units and in 1 case in the administration group of 5 units. This increase in the antibody titer was not observed in the administration group of 1.25 units.

(Comparative Example) Safety Evaluation in Administration of 10 Units

Chondroitinase ABC of 10 units per disk was administered to patients (6 persons) with lumbar disc herniation in the same way as above. As a safety evaluation, (a) the reduction rate in the disc height at week 12 after the administration and (b) the case with the number and incidence rate of vertebral posterior angle of the vertebral body being equivalent to or more than 5 degrees were determined.

The reduction rate in the disc height at week 12 after the administration is shown in FIG. 3. As a result, the average reduction rate in the disc height was 45.4% which was significantly greater than the value (30%) that might produce a problem in safety.

In addition, the results of the vertebral posterior angle of the vertebral body being equivalent to or more than 5 degrees were also shown in Table 1. As shown in Table 1, 33.3% of the patients who showed the vertebral posterior angle of the vertebral body being equivalent to or more than 5 degrees were observed in the administration group of 10 units of chondroitinase ABC. From these results, it is considered that the administration group of 10 units has a high risk related to the instability of the spine.

The volume of the nucleus pulposus in humans and dogs was measured by MRI in order to estimate a dose of chondroitinase ABC effective to humans from the dose of chondroitinase ABC in dogs as described in the Non-Patent Document 4.

(Reference Example) Comparison of Volume of Nucleus Pulposus Using MRI

T2 weighted images were obtained by MRI imaging of the disc between the fourth lumbar vertebra and the fifth lumbar vertebra in 9 healthy volunteers (6 males, 3 females) and resected specimens of dogs (6 animals), and the minor axis, major axis, and area of coronal image of the nucleus pulposus, and the minor axis of sagittal image of the nucleus pulposus were measured. The volume of the nucleus pulposus was calculated (coronal cross-sectional area×sagittal cross-sectional minor axis). The results are shown in Table 2 below.

TABLE 2

| Animal species | Volume of nucleus pulposus (mm$^3$) (Calculated value from MRI image) | Ratio of average volume of nucleus pulposus in MRI image |
| --- | --- | --- |
| Human | 7852.2 ± 2041.2 | Human/dog = 70.2 |
| Dog (Beagle) | 111.8 ± 70.3 | |

Value = Average ± Standard deviation

5. Summary

The incidence rate of showing the vertebral posterior angle of the vertebral body being equivalent to or more than 5 degrees was 33.3% when 10 units of chondroitinase ABC were administered, whereas it was found that such an incidence rate could be significantly reduced to 2% when a half dose, i.e. 5 units were administered.

In addition, while the average reduction rate of the disc height also reached even 45.4% when 10 units of chondroitinase ABC were administered, the reduction rate of the disc height was 17.6% in the administration group of 5 units of chondroitinase ABC. Thus, it was shown that the reduction in the disc height could be remarkably suppressed by decreasing the dose from 10 units to the half dose, i.e. 5 units.

The Non-Patent Document 3 describes that when 0.5 unit of chondroitinase ABC per disk was administered into the human disk, a rapid amelioration in leg pain did not occur, indicating that 0.5 unit was a less dose, but detailed studies on the adverse side effects were not performed and the clinically effective dose was unknown.

By administering chondroitinase ABC in a range of 1-8 units per disk, preferably 1-5 units per disk in accordance with the present invention, it is possible to reduce the adverse side effects while exhibiting a significant amelioration in pain in only a single dose. Further, it was found that by selecting an administration of chondroitinase ABC in the range of 1-3 units, the adverse side effects could be further reduced while exhibiting a similar effect in ameliorating pain to a higher dose of 5 units.

On the other hand, Non-Patent Document 4 describes that even when 0.5-1 unit of chondroitinase ABC per disk was administered into a dog disc, rapid reduction of the nucleus pulposus did not occur, indicating that the dose was too small. In addition, Non-Patent Document 6 describes that the setting of scaling is necessary in the analysis of the experimental results in animal models because the behavior of the disc depends on the size of the disc. Then, from the above reference example, it was confirmed that the volume of human nucleus pulposus was 70 times as large as that of dog nucleus pulposus. In view of the descriptions of the Non-Patent Documents 4 and 6 and given that the volume of human nucleus pulposus was much larger than the volume of dog nucleus pulposus, even when 35-70 units, which were 70 times of 0.5-1 unit, of chondroitinase ABC were administered, such a dose was estimated to be not enough.

In this way, the dose for humans estimated from the experimental results in dogs as described in the Non-Patent Document 4 is quite different from the dose that was found in the present invention, and it was extremely difficult to predict an effective dose for humans.

Thus, it was found that adverse side effects could be reduced by the administration of 1-8 units of chondroitinase ABC per disk into a human disk and disc herniation could be treated in only a single dose.

INDUSTRIAL APPLICABILITY

The present invention can provide a therapeutic agent for disc herniation, which has extremely few adverse side effects, can achieve a prolonged pain-ameliorating effect when administered in only a single dose, and can exhibit a high therapeutic effect and high safety in clinical applications.

The invention claimed is:

1. A method for treating lumbar disc herniation, comprising:
injecting a formulation consisting essentially of chondroitinase ABC in an effective amount of 1-3 units per disc in a single dose into a disc of a human patient with disc herniation.

2. The method according to claim 1, wherein the disc of a human patient is a disc where a nucleus pulposus is present and where the disc herniation occurs.

3. The method according to claim 2, wherein the formulation contains at least one ingredient selected from the group consisting of an excipient, a stabilizer, a binder, an emulsifier, an osmotic agent, a buffer, a pH regulator, an isotonic agent, a preservative, a soothing agent and a colorant.

4. The method according to claim 3, wherein the formulation is lyophilized.

5. The method according to claim 1, wherein the effective amount of chondroitinase ABC is 1.25 units per disc.

6. The method according to claim 5, wherein the disc of a human patient is a disc where a nucleus pulposus is present and where the disc herniation occurs.

7. The method according to claim 6, wherein the formulation contains at least one ingredient selected from the group consisting of an excipient, a stabilizer, a binder, an emulsifier, an osmotic agent, a buffer, a pH regulator, an isotonic agent, a preservative, a soothing agent and a colorant.

8. The method according to claim 7, wherein the formulation is lyophilized.

9. The method according to claim 8, wherein the chondroitinase ABC is derived from *Proteus vulgaris*.

10. The method according to claim 9, wherein the formulation contains sucrose and polyethylene glycol 3350.

11. The method according to claim 8, wherein the formulation contains sucrose and polyethylene glycol 3350.

12. A method for treating lumbar disc herniation, comprising:
injecting a formulation that comprises chondroitinase ABC in an effective amount of 1-3 units per disc in a single dose into a disc of a human patient with disc herniation,
wherein chondroitinase ABC is a sole active ingredient for therapeutic effect in lumbar disc herniation of the formulation.

13. The method according to claim 12, wherein the disc of a human patient is a disc where a nucleus pulposus is present and where the disc herniation occurs.

14. The method according to claim 13, wherein the formulation contains at least one ingredient selected from the group consisting of an excipient, a stabilizer, a binder, an emulsifier, an osmotic agent, a buffer, a pH regulator, an isotonic agent, a preservative, a soothing agent and a colorant.

15. The method according to claim 14, wherein the formulation is lyophilized.

16. The method according to claim 12, wherein the effective amount of chondroitinase ABC is 1.25 units per disc.

17. The method according to claim 16, wherein the disc of a human patient is a disc where a nucleus pulposus is present and where the disc herniation occurs.

18. The method according to claim 17, wherein the formulation contains at least one ingredient selected from the group consisting of an excipient, a stabilizer, a binder, an emulsifier, an osmotic agent, a buffer, a pH regulator, an isotonic agent, a preservative, a soothing agent and a colorant.

19. The method according to claim 18, wherein the formulation is lyophilized.

20. The method according to claim 19, wherein the chondroitinase ABC is derived from *Proteus vulgaris*.

21. The method according to claim 20, wherein the formulation contains sucrose and polyethylene glycol 3350.

22. The method according to claim 19, wherein the formulation contains sucrose and polyethylene glycol 3350.

* * * * *

UNITED STATES PATENT AND TRADEMARK OFFICE
CERTIFICATE OF CORRECTION

PATENT NO. : 11,944,670 B2
APPLICATION NO. : 17/589162
DATED : April 2, 2024
INVENTOR(S) : Taiichi Sirogane et al.

It is certified that error appears in the above-identified patent and that said Letters Patent is hereby corrected as shown below:

On the Title Page

Item (56) References Cited, OTHER PUBLICATIONS (Column 2, Line 9), "studing" should read -- studying --.

Page 2, Item (56) References Cited, OTHER PUBLICATIONS (Column 1, Line 63), "Chodroitinase" should read -- Chondroitinase --.

In the Specification

Column 1, Line 34, "anulus" should read -- annulus --.

Column 1, Line 67, "glucosaminoglycan" should read -- glycosaminoglycan --.

Column 5, Line 23, "(M)" should read -- (μM) --.

Signed and Sealed this
First Day of October, 2024

Katherine Kelly Vidal
*Director of the United States Patent and Trademark Office*